United States Patent [19]

Oxman et al.

[11] Patent Number: 5,635,545
[45] Date of Patent: *Jun. 3, 1997

[54] SEMI-THERMOPLASTIC MOLDING COMPOSITION HAVING HEAT-STABLE CUSTOM SHAPE MEMORY

[75] Inventors: Joel D. Oxman; Lani S. Kangas; F. Andrew Ubel, III, all of St. Paul, Minn.

[73] Assignee: Minnesota Mining and Manufacturing Company, St. Paul, Minn.

[*] Notice: The term of this patent shall not extend beyond the expiration date of Pat. No. 5,403,188.

[21] Appl. No.: 388,156

[22] Filed: Feb. 13, 1995

Related U.S. Application Data

[63] Continuation of Ser. No. 137,584, Oct. 15, 1993, Pat. No. 5,403,188, which is a continuation of Ser. No. 484,695, Feb. 23, 1990, abandoned.

[51] Int. Cl.$^6$ .................... A61C 5/08; A61C 5/00
[52] U.S. Cl. .................... 523/115; 522/90; 522/104; 522/908; 528/950; 433/223; 433/218; 433/219
[58] Field of Search ................ 433/223, 218, 433/219; 523/115; 522/90, 104, 908; 528/950

[56] References Cited

U.S. PATENT DOCUMENTS

| | | | |
|---|---|---|---|
| 2,985,961 | 5/1961 | Schwartz | 32/2 |
| 3,382,202 | 5/1968 | Forrester et al. | 260/32.6 |
| 3,427,161 | 2/1969 | Laridon et al. | 96/35.1 |
| 3,647,498 | 3/1972 | Dougherty | 433/218 |
| 3,756,827 | 9/1973 | Chang et al. | 96/86 |
| 3,759,807 | 9/1973 | Osborn et al. | 204/159.23 |
| 3,767,627 | 10/1973 | Schoen | 260/78.3 |
| 4,059,715 | 11/1977 | Pletcher | 428/349 |
| 4,071,424 | 1/1978 | Dart et al. | 204/159.15 |
| 4,182,829 | 1/1980 | Walkowiak et al. | 528/75 |
| 4,227,877 | 10/1980 | Tureaud et al. | 433/37 |
| 4,240,415 | 12/1980 | Wartman | 128/90 |
| 4,327,013 | 4/1982 | Peters | 524/538 |
| 4,330,283 | 5/1982 | Michl et al. | 433/218 |
| 4,361,528 | 11/1982 | Ginsburg et al. | 264/168 |
| 4,433,958 | 2/1984 | Fellman et al. | 433/219 |
| 4,445,854 | 5/1984 | Bekey et al. | 433/37 |
| 4,483,333 | 11/1984 | Wartman | 128/90 |
| 4,491,453 | 1/1985 | Koblitz et al. | 523/115 |
| 4,552,906 | 11/1985 | Podszun et al. | 523/115 |
| 4,569,342 | 2/1986 | von Nostitz | 128/136 |
| 4,642,126 | 2/1987 | Zador et al. | 51/295 |
| 4,659,786 | 4/1987 | Kawakami et al. | 525/415 |
| 4,678,435 | 7/1987 | Long | 433/218 |
| 4,740,245 | 4/1988 | Futami et al. | 106/35 |
| 4,761,136 | 8/1988 | Madhaven et al. | 522/90 |
| 4,768,951 | 9/1988 | Abiru et al. | 433/48 |
| 4,776,792 | 10/1988 | Wagner et al. | 433/71 |
| 4,787,850 | 11/1988 | Michl et al. | 523/115 |
| 4,828,583 | 5/1989 | Oxman et al. | 51/295 |
| 4,835,203 | 5/1989 | Sieverding | 524/277 |
| 4,859,742 | 8/1989 | Pattein et al. | 525/131 |
| 4,867,680 | 9/1989 | Harc et al. | 433/37 |
| 4,912,174 | 3/1990 | Grouiller | 525/415 |
| 4,952,614 | 8/1990 | Reiners et al. | 523/115 |
| 5,011,407 | 4/1991 | Pelerin | 433/48 |
| 5,028,667 | 7/1991 | McLain et al. | 525/415 |
| 5,066,231 | 11/1991 | Oxman et al. | 433/48 |
| 5,403,188 | 4/1995 | Oxman et al. | 433/218 |

FOREIGN PATENT DOCUMENTS

| | | |
|---|---|---|
| 0096020 | 12/1983 | European Pat. Off. . |
| 0173085 | 7/1984 | European Pat. Off. . |
| 150952 | 8/1986 | European Pat. Off. . |
| 2078675 | 11/1971 | France . |
| 3810907 | 10/1988 | Germany . |
| 63-171554 | 8/1978 | Japan . |
| 63-270759 | 7/1979 | Japan . |
| 1304112 | 8/1983 | United Kingdom . |
| 83/02898 | 9/1983 | WIPO . |
| WO9014052 | 11/1990 | WIPO . |
| WO94/07429 | 4/1994 | WIPO ............... A61C 13/00 |

OTHER PUBLICATIONS

Tone® P-300 and P-700 High Molecular Weight Caprolactone Polymers (1988 pro literature of Union Carbide Corp.).
Chem. Abs. 95:225704U.
Aqueron® bite registration sticks and custom tray material (cover letter dated 8 Dec. 1989 form E. M. Natt Ltd. with brochure from Erkodent Comp.
Patent Abstract of Japanese Publication No. JP-A-12 69 613, published Oct. 26, 1989.

*Primary Examiner*—Andrew E. C. Merriam
*Attorney, Agent, or Firm*—Gary L. Griswold; Walter N. Kirn; Dale A. Bjorkman

[57] ABSTRACT

Thermoplastic molding compositions are made from a mixture of thermoplastic material (for example, polycaprolactone), a free-radically polymerizable resin (for example, a urethane diacrylate oligomer), and free-radical initiator (for example, a visible-light cure photoinitiator). The mixture is solid at 38° C., has a melting or softening point that comfortably can be withstood by oral tissues, and can be imprinted with a heat-stable custom shape memory and semi-thermoplastic properties by shaping the composition to a desired shape and then causing or permitting the resin to undergo polymerization.

12 Claims, 3 Drawing Sheets

SEMI-THERMOPLASTIC MOLDING COMPOSITION HAVING HEAT-STABLE CUSTOM SHAPE MEMORY

This application is a continuation of U.S. Ser. No. 08/137,584 filed Oct. 15, 1993, now U.S. Pat. No. 5,403,188, which in turn is a continuation of U.S. Ser. No. 07/484,695, filed Feb. 23, 1990, now abandoned.

FIELD OF THE INVENTION

This invention relates to thermoplastic molding compositions. It also relates to dental impression-taking, to the manufacture of dentures, crowns, bridges and other oral prosthetic devices, and to general-purpose modelmaking.

BACKGROUND OF THE INVENTION

High molecular weight poly (epsiloncaprolactone) (also known as "polycaprolactone") has been used as a thermoplastic molding compound for general-purpose modelmaking and dentistry. References describing polycaprolactone molding compositions include U.S. Pat. No. 4,835,203, Kokat (Japanese Published Pat. Appl.) Nos. 63-171554 and 63-270759, and TONE® POLYMERS P-300 AND P-700 High Molecular Weight Caprolactone Polymers (1988 product literature of Union Carbide Corp.). The polycaprolactone described in Kokai No. 63-171554 is said to be polymerized in the presence of a small amount of epoxy resin, which is said to improve the hydrolysis resistance of the polycaprolactone.

Deldent Dental Supplies Co., Ltd. sells a heat-softenable custom tray material referred to as the "formable base impression" or "FBI" denture tray system. The FBI tray is immersed in hot water to soften the tray, placed in a patient's mouth while warm and shaped to conform to the patient's arch. The FBI tray is said to return to its original configuration if immersed again in hot water.

U.S. Pat. Nos. 4,240,415 and 4,483,333 describe radiation-crosslinked polycaprolactone orthopedic casts. The patents refer to the possible inclusion of "chemicals containing two or more double bonds in each molecule". The casts are radiation-crosslinked using several 5 megarad exposures in an electron beam apparatus.

SUMMARY OF THE INVENTION

The above-described thermoplastic molding compositions lack heat-stable custom shape memory. In other words, when the compositions are heated, formed into a desired or "custom" shape, then cooled, the resulting model does not have a permanent memory for the custom shape. When reheated, the warmed model may undergo creep and distortion, or even melt completely. When the tray is reheated, it is said to return to its original (non-custom) shape. Accordingly, heat can cause the desired custom shape to be obliterated or undesirably distorted.

We believe that no previous commercially-available thermoplastic dental molding compositions have provided heat-stable custom shape memory (for brevity, "hot custom memory"). The molding compositions of our invention have hot custom memory, and it is manifested by a semi-permanent shape memory that can be deliberately imparted to (or imprinted on) the composition by the user. The memory has heat resistance that overcomes the normal thermoplastic behavior of the composition before the memory is imprinted. Accordingly, the compositions can be said to be semi-thermoplastic rather than thermoplastic.

The present invention provides a molding composition useful for dental impressioning and general-purpose modelmaking, comprising a homogeneous blend of a thermoplastic material (for example, polycaprolactone), a free-radically polymerizable resin (for example, a urethane diacrylate oligomer), and a free-radical initiator (for example, a visible-light photoinitiator), the blend being solid at 38° C. and having a melting or softening point that comfortably can be withstood by oral tissues, the composition having semi-thermoplasticity and hot custom memory after the resin is polymerized.

The invention also provides a method for making an impression of dental tissue, comprising the steps of a) enveloping the tissue with a molten or softened molding composition comprising the above mentioned homogeneous blend, and, in either order, b) cooling the composition so that it solidifies and c) causing or permitting the free-radically polymerizable resin to undergo polymerization, whereby a semi-thermoplastic dental tissue impression having hot custom memory is obtained.

The molding compositions of the invention have improved physical properties in both the warm and cool states, especially when a custom-molded shape prepared from a composition of the invention is accidentally or intentionally subjected to elevated temperatures.

DETAILED DESCRIPTION

Figure 1:
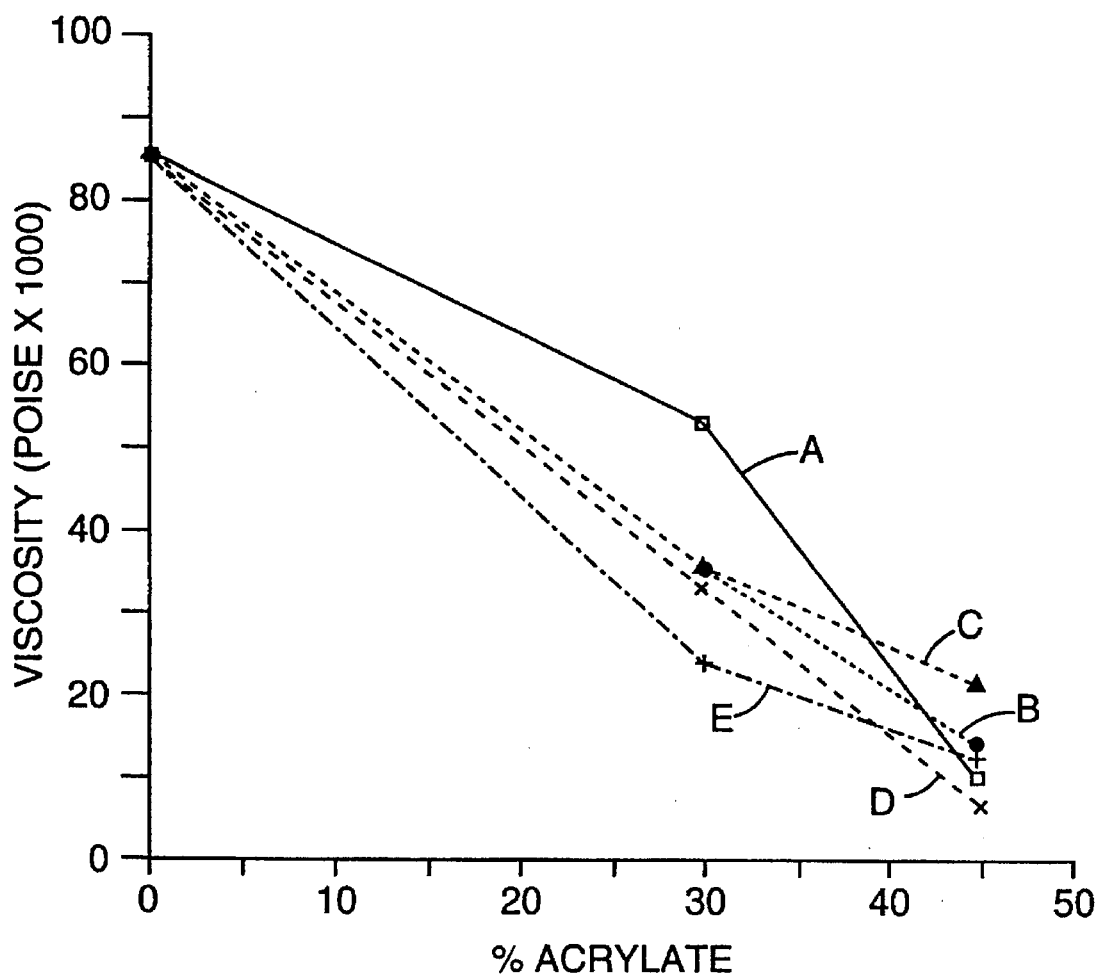
FIG. 1 is a plot of viscosity vs. percent acrylate resin for the compositions of Runs 1–11 of EXAMPLE 1.

A variety of thermoplastic materials can be used in the molding compositions of the invention. Selection of the thermoplastic material should be based in part on the desired end use for the molding composition and the desired properties of the composition in the molten or softened ("warm") and solid ("cool") states. The warm state is characterized by appreciable mass flow of the molding composition under moderate (hand) pressure at some temperature between body temperature (about 38° C.) and the maximum temperature that comfortably can be withstood by oral tissues. This maximum temperature is generally thought to be about 75° C., although a maximum of about 65° C. is preferred. The cool state is characterized by sufficient strength and stiffness to permit an acceptably accurate dental impression to be made from the molding composition, and by minimal apparent mass flow of the molding composition under moderate pressure at temperatures below 38° C.

The warm and cool state properties permit the molding composition to be heated to a moderate temperature, manually shaped in the mouth while warm to conform to the shape of hard and soft oral tissue, and cooled within the mouth to form a substantially rigid model.

Representative thermoplastic materials include polyesters and polyurethanes such as those described in U.S. Pat. Nos. 3,382,202, 4,059,715, 4,182,829, 4,327,013, 4,361,538, 4,552,906 and 4,569,342, and copolymers such as those described in U.S. Pat. Nos. 4,659,786, 4,740,245 and 4,768, 951. The thermoplastic material preferably is a homopolymer or copolymer of epsilon-caprolactone. The polycaprolactone optionally can contain property-modifying or crosslinkable functional groups (for example hydroxyl, acrylate, methacrylate, epoxy, isocyanato or vinyl groups) if desired.

Preferred polycaprolactones have the formula:

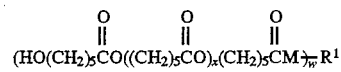

where $R^1$ is an aromatic or a straight chain or branched aliphatic backbone, which can optionally contain one or more non-interfering substituents such as hydroxyl or amine groups, w is 1 if $R^1$ is hydrogen, and w otherwise has an average value of about 1 to about 4, M is oxygen or $-NR^2-$ where $R^2$ is hydrogen or a non-interfering aromatic or aliphatic group, and the product of w times x is greater than about 35.

Blends of polycaprelactones can also be employed. Suitable polycaprolactone blends are described in our copending application Serial No. (Attorney's Docket No. 44686 USA 1A), the disclosure of which is incorporated in this specification by reference.

Preferred commercially available polycaprolactone polymers include "TONE P-700" and "TONE P-767" (40,000 molecular weight) and "TONE P-300" (10,000 molecular weight) polycaprolactone from Union Carbide Corp., and the "CAPA" polycaprolactones "630" (30,000 molecular weight), "640" (40,000 molecular weight), "650" (50,000 molecular weight), and "656" (56,000 molecular weight) from Interox.

The free-radically polymerizable resin contains at least one ethylenically unsaturated monomer, oligomer, or polymer capable of undergoing addition polymerization. Suitable monomers include mono-, di- or polyfunctional acrylates and methacrylates such as methyl acrylate, methyl methacrylate, ethyl acrylate, isopropyl methacrylate, n-hexyl acrylate, styryl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,3-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis(1-(2-acryloxy))-p-ethoxyphenyldimethylmethane, bis(1-(3-acryloxy-2-hydroxy))-p-propoxyphenyldimethylmethane, tris-hydroxyethylisocyanurate triacrylate, beta-methacrylaminoethyl methacrylate, and mixtures thereof. Other suitable monomers include unsaturated amides such as methylene bis-acrylamide, methylene bis-methacrylamide, 1,6-hexamethylene bis-acrylamide and diethylenetriamine tris-acrylamide. Suitable oligomeric or polymeric resins include 200 to 500 molecular weight polyalkylene glycols, acrylated or methacrylated oligomers such as those of U.S. Pat. No. 4,642,126, acrylated urethanes such as "SARTOMER" 9503, 9504 and 9505 (Sartomer Corp.), "INTEREZ" CMD 8803, 8804 and 8805 (Radcure Specialties, Inc.), and "PHOTOMER" 6060, 6110 and 6160 (Henkel Corp.), as well as acrylated polyester oligomers such as "EBERCRYL" 830 (Radcure Specialties, Inc.). Mixtures of free-radically polymerizable monomers, oligomers or polymers can be used if desired.

The free-radically polymerizable resin can if desired be cured using a conventional chemical initiator system, such as a combination of a peroxide and an amine. However, chemical cure initiator systems typically require at least partial ingredient separation before use. The resin is preferably cured using a photoinitiator, optionally combined with a suitable photosensitizer or accelerator. The photoinitiator should be capable of generating free radicals for addition polymerization at some wavelength between 200 and 800 nm. Suitable photoinitiators include alpha-diketones, monoketals of alpha-diketones or ketoaldehydes, acyloins and their corresponding ethers, chromophore-substituted halomethyl-s-triazines, chromophore-substituted halomethyl-oxadiazoles, aryliodonium salts, and other commercially available ultraviolet ("UV") and visible light photoinitiators. Preferred photoinitiator systems include a mono or diketone photoinitiator together with a suitable donor compound or accelerator, such as the systems described in U.S. Pat. Nos. 3,427,161, 3,756,827, 3,759,807, 4,071,424, 4,828,583, U.K. Pat. Specification No. 1,304, 112, European Published Pat. Appl. No. 150,952 and Chem. Abs. 95:225704U.

The molding compositions of the invention can contain a wide variety of adjuvants depending upon the desired end use. Suitable adjuvants include solvents, diluents, plasticizers, pigments, dyes, inorganic or organic fibrous or particulate reinforcing or extending fillers, thixotropic agents, indicators, inhibitors, stabilizers, UV absorbers, medicaments (e.g., leachable fluorides), biocides and the like. For custom tray applications, the molding composition preferably contains one or more fillers that limit the composition's 60° C. relaxation stress at equilibrium, as described in our copending application Serial No. (Attorney's Docket No. 45066 USA 3A), the disclosure of which is incorporated in this specification by reference.

The types and amounts of ingredients in the molding compositions of the invention usually will be empirically selected. The thermoplastic material and free-radically polymerizable resin preferably are present in "major proportion" and "minor proportion", respectively. By this we mean that the composition preferably contains a higher weight percent of thermoplastic material than of polymerizable resin.

The composition should remain substantially homogeneous (that is, it should not undergo macroscopic phase separation or filler sedimentation). Subject to the effects of any imprinted hot custom memory, the composition preferably should retain its desired physical properties even if repeatedly cycled between the warm and cool states. Thus the selection of ingredients can be guided in part by the desire to preserve homogeneity and thermal reversibility. Also, the amount of polymerizable resin and initiator should be sufficient to provide the desired degree of hot custom memory. Lower amounts of resin tend to increase susceptibility to creep after the custom memory has been imparted to the composition. Higher resin amounts tend to decrease elasticity.

As a further guide, the preferred amounts of thermoplastic material, polymerizable resin, initiator and filler for dental impressioning are as follows:

| Ingredient | Preferred Weight % |
|---|---|
| Thermoplastic material | up to 90 |
| Polymerizable resin | up to 50 |
| Initiator | up to 10 |
| Filler | 0–70 |

The ingredients in the molding composition can be blended by hand or by mechanical mixing. The ingredients preferably are warmed sufficiently to melt the thermoplastic material, but if desired can be mixed at lower temperatures. Any suitable mixing device can be used, including kettles equipped with a mechanical stirrer, extruders, rubber mills, and the like.

The molding composition can be put up in a variety of forms including preformed sheets, arch-shaped trays, ropes, buttons, woven or non-woven webs and the like. The composition can be shaped in a variety of ways including extrusion, injection molding and web processing using a coating knife or rollers. The composition can be sold unwrapped, loosely wrapped in a package, or packaged in tubes, syringes, flexible outer plastic skins, plastic or metal trays and the like. The composition can be extruded or cast in mono-, bi-, or poly-layers (for example, aplanar layers or layers arranged in core-shell fashion) in which each layer has a selected melting temperature, viscosity, modulus, stickiness, or other desired physical properties.

The molding composition can be converted from the cool state to the warm state by using a variety of energy sources. The composition can be immersed in a heated bath containing a suitable inert liquid (for example, water or a fluorochemical fluid) that will not dissolve or swell the composition in either its cool or warm states. The composition can also be softened using heat sources such as a hot air gun, hot plate, conventional oven, infrared heater or microwave oven. The composition can be encased in a plastic pouch, syringe or other container which is in turn heated (e.g. electrically), or subjected to one or more of the above-mentioned heating methods.

Transforming the molding composition from a warm state to a cool state requires loss of thermal energy and can be carried out using a variety of cooling techniques. Cooling can take place under ambient conditions in the presence of air only. Cooling can be expedited using forced air, cold water, ice, or heat sinks such as chilled "cold packs" or flexible pouches containing low boiling inert liquids. Of particular interest for both dental and orthopedic applications are chilled cold packs in flexible pouches that have been preshaped to match the contours of the model being cooled. For example, flexible pouches containing a chilled coolant can be fabricated in the shape of a full arch or quadrant and placed intraorally in contact with the warm molding composition. Analogously, a large coolant-filled blanket can be draped around an orthopedic casting or splint material prepared from a molding composition of the invention.

Hot custom memory is imparted to the molding composition by allowing or causing the free-radically polymerizable resin and initiator to harden (for example, by exposing a composition containing a photoinitiator to a suitable light source). Polymerization can take place before or after the warmed, softened model is allowed to cool, although carrying out polymerization after cooling will tend to lengthen polymerization times. After polymerization, the model preferably retains sufficient elasticity to permit it to be removed from undercut surfaces such as the undercuts typically found in the oral cavity.

The polymerized, cooled model will exhibit hot custom memory. Accordingly, it will be more resistant to heat and handling stresses than models made from the thermoplastic material alone. If the model is accidentally distorted, it can be returned to its custom shape by reheating it in a relaxed condition. For example, the model can be immersed in a hot water bath and removed for cooling after the custom shape has reappeared. While still in the warm state, it will remain pliable, and accordingly will exhibit semi-thermoplasticity. This permits the custom shape to be adjusted if desired.

A simplified dental impression system can be prepared from the molding composition. Traditional impressioning systems employ one or more low viscosity, flowable elastomeric materials such as an alginate, hydrocolloid, polyvinylsiloxane, polyether, or polysulfide contained in a fairly rigid adhesive-coated plastic or metal arch-shaped tray. The elastomeric material often is applied both to the dental tissue to be modeled and to the tray. The elastomeric material and surrounding tray are subsequently pressed against the dental tissue, and left in place until the elastomeric material has hardened. This traditional process involves several materials and steps, material waste and fairly lengthy set times.

The present invention permits impressioning using a monolayer or a bilayer thermoplastic molding composition. The monolayer model, or at least one layer of the bilayer model, is made from a molding composition of the invention. In a preferred embodiment, a flat sheet or a preformed arch-shaped tray is made from two coextruded thermoplastic layers. The physical properties of each layer emulate in part the properties of a conventional rigid tray and the elastomeric material respectively. At a suitable elevated temperature the "tray" layer becomes a conformable, non-sticky melt (thereby permitting the warm tray layer to be hand-shaped into a custom tray configuration) and the "elastomer" layer exhibits good flow and low viscosity (thereby permitting the warm elastomer layer to flow around tooth structure and provide an accurate model). The warm bilayer construction provides easy placement, accurate impressioning, and efficient use of materials. Cooling can take place rapidly, and in less time than is required to harden a conventional impression. Once cooled, the tray layer exhibits sufficient rigidity to discourage distortion of the impression during removal from the mouth or during subsequent handling. If the tray layer is made from a molding composition of the invention and is polymerized after the desired custom shape has been attained, then the hot custom memory properties of the tray layer discourage creep and distortion. The elastomer layer provides stable, accurate modeling of hard and soft dental tissue. If the elastomer layer is made from a molding composition of the invention, then the hot custom memory properties of the elastomer layer aid in making accurate casts using heated gypsum stone substitutes such as hot-melt thermoplastics. In either embodiment, the model can be shipped through the mail and exposed to elevated temperatures with reduced risk that the model will melt or otherwise become permanently distorted.

If desired, a custom impression tray can be formed from a molding composition of the invention and filled with a conventional elastomeric impression material (for example, a silicone elastomer). By shaping the tray in the mouth before (or if desired, after) it is filled with elastomer, the tray volume and required amount of elastomer will be minimized.

The molding compositions of the invention have many other uses. For example, they can be used to prepare crowns, bridges, dentures, splints and pontics. They can also be used to prepare shapeable orthopedic casts and splints. They can be used in modelmaking, for example in tool and die-making. They will find general use in applications requiring rapid, accurate shaped object formation.

The following examples are offered to aid in understanding the invention and are not to be construed as limiting its scope. Unless otherwise indicated, all parts and percentages are by weight.

EXAMPLE 1

70 Parts "TONE P-767" (40,000 molecular weight) polycaprolactone and 30 parts "SR-9503" urethane diacrylate oligomer were placed in an open vessel and heated in an oven at 80° C. until both components were fluid. The vessel was transferred to an 80° C. water bath and the mixture stirred until homogeneous. While working under a safelight, 0.50 parts camphorquinone ("CPQ") and 0.50 parts p-ethyldimethylaminobenzoate ("EDMAB") were dissolved in the mixture with stirring. The resultant blend was poured onto polyester sheeting atop a horizontal platform. A second polyester sheet was placed atop the molten mass. A roller was used to form the blend into sheets of approximately 2–4 mm thickness. The sheets were transparent while warm and became opaque when cooled under a stream of cold water.

Using a similar procedure a control composition (containing 100% polycaprolactone) and fifteen additional polycaprolactone/acrylate blends were prepared. Set out below in TABLE I are the types and amounts of polycaprolactone ("PCL") and acrylate in each composition, and several physical properties for each composition. Warm state viscosity was measured at 65° C. using a rheometric dynamic analyzer (Rheometrics, Inc.) operated at 20% maximum strain and 1 radian/second strain rate.

composition samples were irradiated while cold. The clamp and solidified molding composition were removed from the die. The resulting model was stored at 23±1° C. and 50±5% relative humidity for 24 hours. Dimensional stability was determined by comparing the distances between the ruled lines on the model and on the ruled die using an optical comparator.

TABLE I

| Run no. | PCL Type | PCL Parts | Acrylate Type | Acrylate Parts | Viscosity 65° C. kilopoise | Modulus, 30° C. dyne/cm² × 10⁸ | | | Dimensional stability, % shrinkage | | |
|---|---|---|---|---|---|---|---|---|---|---|---|
| | | | | | | NIR[2] | IR Cold[3] | IR Hot[4] | NIR | IR Cold | IR Hot |
| 1 | P-767[1] | 100 | None | 0 | 85.0 | 11.7 | NM[5] | NM | 0.70 | NM | NM |
| 2 | " | 70 | SR-9503[6] | 30 | 52.7 | 4.2 | 7.8 | 5.5 | 0.47 | 0.49 | 0.55 |
| 3 | " | 55 | " | 45 | 9.2 | 0.9 | 5.2 | 5.6 | NV | 0.40 | 0.45 |
| 4 | " | 70 | SR-9504[8] | 30 | 35.1 | 5.9 | 4.9 | 4.5 | 0.54 | 0.58 | 0.53 |
| 5 | " | 55 | " | 45 | 12.8 | 3.3 | 4.3 | 8.3 | 0.57 | 0.57 | 0.51 |
| 6 | " | 70 | SR-9505[9] | 30 | 35.0 | 6.1 | 11.0 | 9.2 | 0.58 | 0.56 | 0.49 |
| 7 | " | 55 | " | 45 | 20.4 | 3.8 | 10.0 | 13.9 | NV | 0.28 | 0.41 |
| 8 | " | 70 | CMD-8803[10] | 30 | 32.8 | 0.01 | 6.2 | 9.7 | 0.51 | 0.35 | 0.46 |
| 9 | " | 55 | " | 45 | 6.2 | 0.8 | 6.4 | 4.8 | NM | 0.34 | 0.41 |
| 10 | " | 70 | CMD-8805[11] | 30 | 23.6 | 9.1 | 24.1 | 16.9 | 0.57 | 0.69 | 0.70 |
| 11 | " | 55 | " | 45 | 11.3 | 3.8 | 0.2 | 31.3 | 0.38 | 0.66 | 0.73 |
| 12 | " | 70 | 230[12] | 30 | 11.4 | 7.6 | 8.2 | 7.3 | NV | 0.41 | 0.50 |
| 13 | " | 55 | " | 45 | 15.4 | 5.6 | 5.7 | 6.7 | NV | 0.25 | 0.44 |
| 14 | " | 70 | 4287[13] | 30 | 12.7 | 6.1 | 9.2 | 8.6 | 0.43 | 0.59 | 0.58 |
| 15 | " | 55 | " | 45 | 4.9 | 4.1 | 6.3 | 4.5 | 0.39 | 0.53 | 0.49 |
| 16 | " | 70 | 830[14] | 30 | 0.1 | 0.03 | 19.0 | 11.6 | 0.32 | 0.83 | 0.63 |
| 17 | " | 55 | " | 45 | 0.03 | NM | 12.7 | 5.5 | 0.23 | 1.01 | 1.16 |

[1]"TONE P-767" 40,000 molecular weight polycaprolactone (Union Carbide Corp.).
[2]"NIR" - Not irradiated.
[3]"IR Cold" = Irradiated cold.
[4]"IR Hot" = Irradiated hot.
[5]"NM" = Not measured.
[6]"SR-9503" urethane diacrylate oligomer (Sartomer Corp.).
[7]"NV" = Measurement attempted but not recorded due to poor die reproduction.
[8]"SR9504" urethane diacrylate oligomer (Sartomer Corp.).
[9]"SR-9505" urethane diacrylate oligomer (Sartomer Corp.).
[10]"CMD-8803" urethane diacrylate oligomer (Radcure Specialties, Inc.).
[11]"CMD-8805" urethane diacrylate oligomer (Radcure Specialties, Inc.).
[12]"Ebercryl 230" Urethane acrylate (Radcure Specialties, Inc.).
[13]"Ebercryl 4287" Aromatic urethane acrylate (Radcure Specialties, Inc.).
[14]"Ebercryl 830" polyester hexacrylate (Radcure Specialties, Inc.).

Cool state storage modulus was measured at 30° C. on the rheometric dynamic analyzer, operated at 1.4% maximum strain and a 10 radian/second strain rate, on samples subjected to several curing conditions. The samples were 1) not irradiated 2) irradiated under "cold" conditions while the sample was at 25° C. in a custom-molded configuration, using a "VISILUX 2" dental curing lamp (3M) operated for two minutes, or 3) irradiated under "hot" conditions while the sample was at about 50°–55° C. in a custom-molded configuration, using the same lamp and time as in 2). These three conditions are identified as "NIR", "IR Cold", and "IR Hot" in the tables that follow.

Dimensional stability was evaluated using a modified version of American Dental Association (ADA) Test Specification No. 19 (J.A.D.A., 94, 733 (1977)). Each molding composition was heated to 80° C. until molten and poured onto the ruled die prescribed in the Test Specification. A transparent rigid plate was placed atop the molten composition, and secured to the ruled die with a clamp. Selected samples of the composition were left unirradiated or irradiated while hot. The molten composition was allowed to cool for 5 minutes at room temperature. Selected molding The above data illustrates the extent to which a reduction in warm state viscosity, an increase in cool state modulus, and a reduction in shrinkage can be attained by blending polycaprolactone with free-radically polymerizable resin and photoinitiator, and irradiating the blend under hot or cold conditions. The data is further illustrated in FIGS. 1 and 2. FIG. 1 shows an unsmoothed plot of viscosity at 65° C. vs. percent polymerizable resin for Runs 1–11 of TABLE I. Curves A through E connect the data points for blends containing the polymerizable resins "SR-9503", "SR-9504", "SR-9505", "CMD-8803" and "CMD-8805", respectively.

Figure 2:
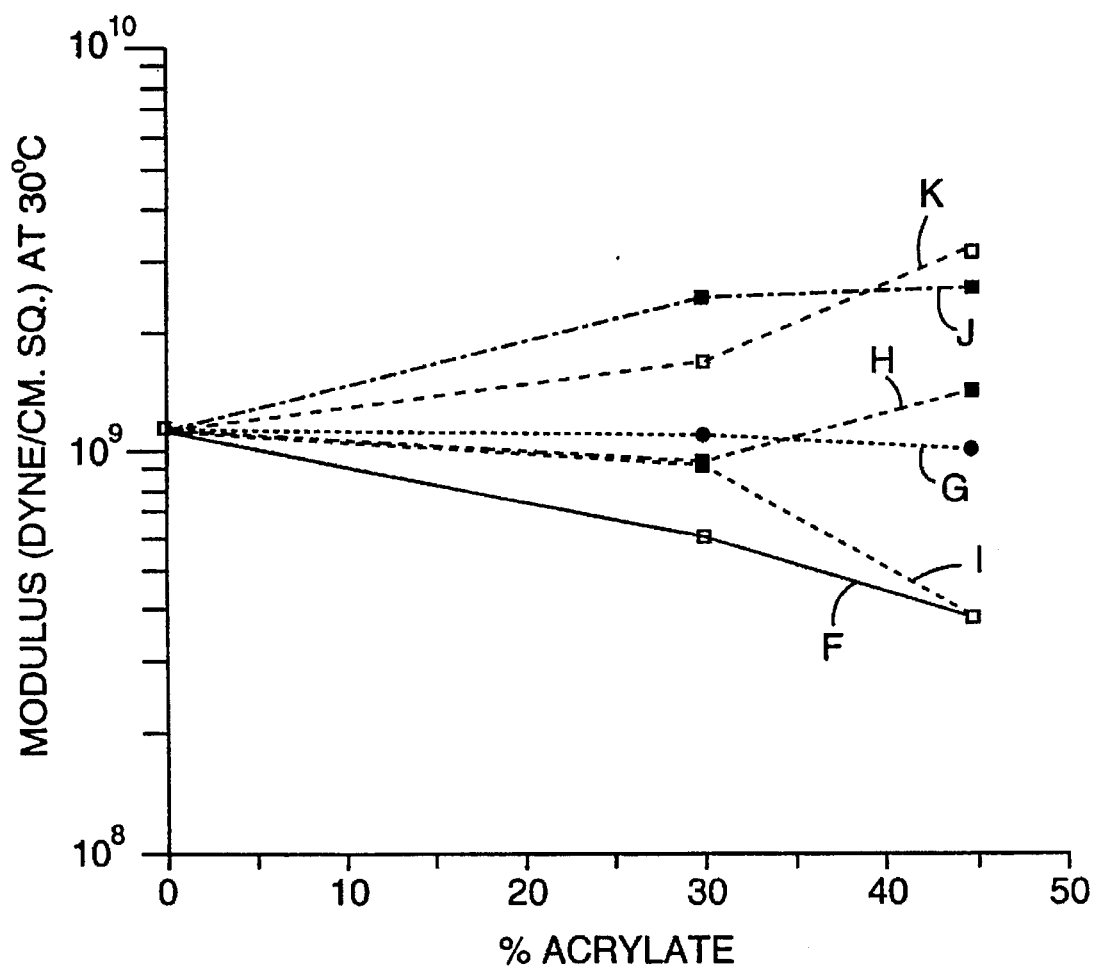
FIG. 2 is a plot of storage modulus vs. percent acrylate resin for the compositions of Runs 1, 6, 7, 10 and 11 of EXAMPLE 1.

FIG. 2 shows an unsmoothed plot of storage modulus at 30° C. vs. percent polymerizable resin for the compositions of Runs 1, 6, 7, 10 and 11. Curves F, G, and H are for compositions containing "SR-9505" polymerizable resin (Runs 6 and 7) in the unirradiated, irradiated cold and irradiated hot conditions, respectively. Curves I, J and K are for compositions containing "CMD-8805" polymerizable resin (Runs 10 and 11) in the unirradiated, irradiated cold and irradiated hot conditions, respectively. As shown by the curves, the irradiated compositions exhibited improved modulus compared to unirradiated compositions.

Figure 3:
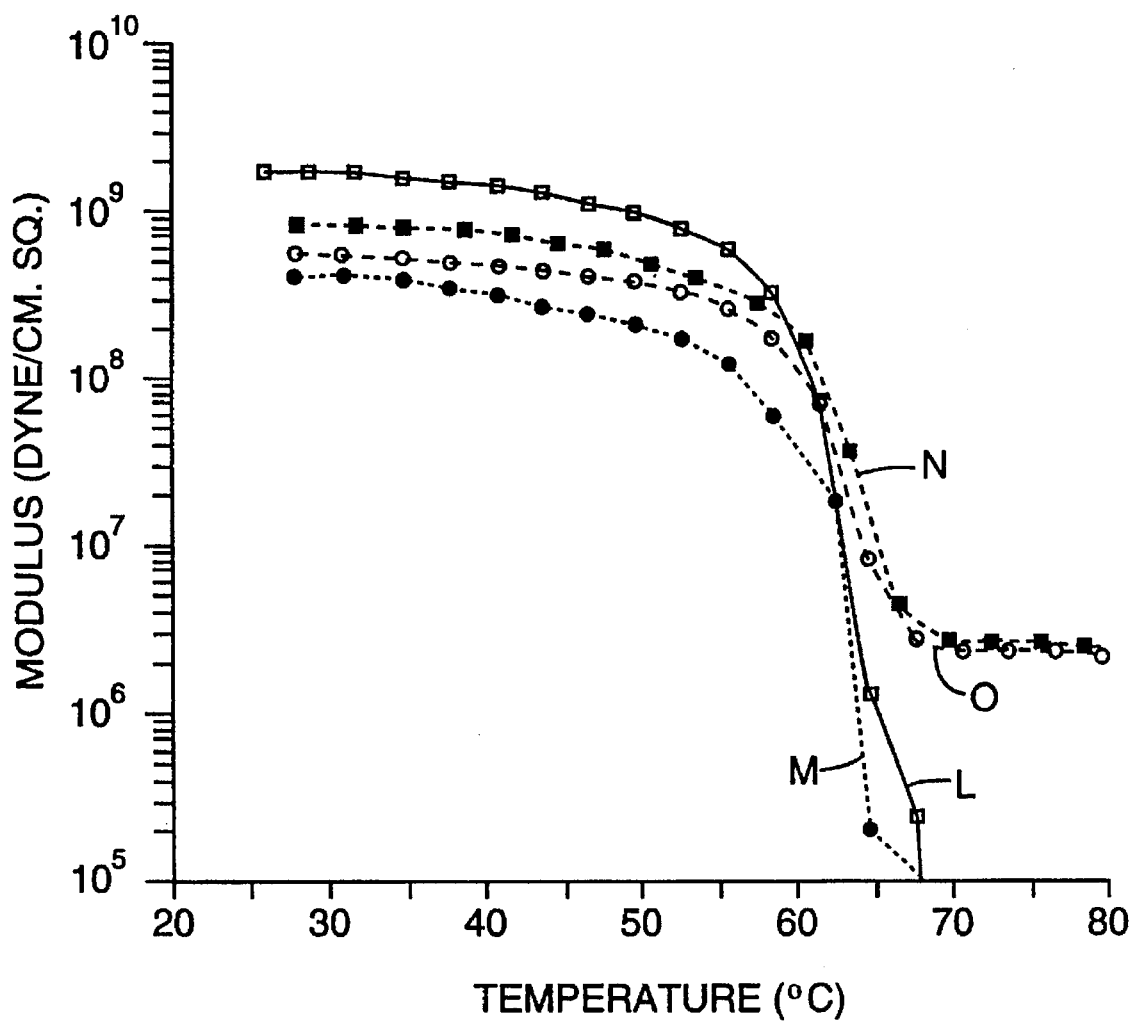
FIG. 3 is a plot of storage modulus for the compositions of Runs 1 and 2 of EXAMPLE 1, showing the effect of imparting hot custom memory to the composition of Run 2 under various conditions.

Referring now to FIG. 3, an unsmoothed plot of storage modulus vs. temperature is shown for Run 1 (curve L) and Run 2 (curves M, N and O) of TABLE I. The measurements were made using a rheometric dynamic analyzer operated at 1.4% maximum strain and a 10 radians/second strain rate. Curve L is a control, and illustrates the substantial decrease in modulus that occurs when the temperature of the molding composition exceeds its melting or softening temperature. Curves M through O illustrate the modulus of a polycaprolactone/polymerizable resin blend in the unirradiated, irradiated cold and irradiated hot conditions, respectively. As shown by curves N and O, modulus remains high and is relatively unaffected by temperature. These compositions thus have significantly improved heat resistance.

EXAMPLE 2

20 Parts "IMSIL A-25" ground quartz filler (Illinois Minerals) were added with stirring to an open vessel containing 24.5 parts "CMD-8805" urethane acrylate oligomer, 0.5 parts CPQ and 1.0 parts EDMAB. The mixture was stirred at 80° C. until homogeneous. 54 Parts "TONE P-767" polycaprolactone were added to the vessel, and the mixture was heated with stirring at 80° C. until molten.

Using a similar procedure, a control composition containing no filler and eight additional compositions containing various types and amounts of fillers were prepared. Set out below in TABLE II are the amounts of polycaprolactone ("PCL") and polymerizable resin ("Resin") in each composition, the type and amount of filler in each composition, and the modulus for compositions that were not irradiated ("NIR") or irradiated while cold ("IR Cold").

TABLE III-continued

| Ingredient | Parts |
|---|---|
| Antimony oxide | 0.10 |

[1]"POLYMEG 2000" (Quaker Oats Chemical).
[2]"IRGANOX 1010" (Ciba Geigy Corp.).

The "POLYMEG 2000" diol and 1,6-hexanediol were transferred to a three neck flask fitted with a mechanical stirrer, condenser, "Dean-Stark" trap, heating mantle, thermometer and nitrogen inlet. The diols were stirred at moderate speed under a nitrogen purge for 5–10 minutes while heating to a temperature of 100° C. Adipic acid was slowly added and the mixture heated to a temperature of about 140°–150° C. Water began collecting in the trap. The reaction was continued until at least 80% complete on the basis of water volume collected. The reaction mixture was cooled to 150° C. and the trap removed. The antioxidant and antimony oxide were then added to the flask. The flask was purged with nitrogen for 5 minutes. Following the purge, the flask was attached to a vacuum line and the pressure reduced while maintaining a reaction temperature of 150° C. After 30 to 60 minutes a vacuum of <0.1 mm Hg was attained and the reaction temperature increased to 230° C. The reaction was continued until the acid number had decreased to less than <1 mg KOH gm sample. The resulting semi-crystalline thermoplastic composition contained about 53% amorphous segment content and exhibited rubbery, elastomeric properties in the solid state.

A blend of this segmented polyester and a free-radically polymerizable acrylate resin ("CMD-8803", Interez) was

TABLE II

| Run no. | Ingredients | | | | Modulus, 30° C., dyne/cm² × 10⁸ | |
|---|---|---|---|---|---|---|
| | PCL Amount | Resin Amount | Filler Type | Amount | NIR | IR cold |
| 1 | 74.0 | 24.5 | — | — | 3.2 | 8.1 |
| 2 | 54.0 | 24.5 | "IMSIL"[1] | 20 | 5.1 | 7.1 |
| 3 | 39.0 | 19.5 | " | 40 | NM[2] | 2.8 |
| 4 | 54.0 | 24.5 | "VICRON"[3] | 20 | 1.5 | 8.6 |
| 5 | 39.0 | 19.5 | " | 40 | NM | 9.1 |
| 6 | 54.0 | 24.5 | "DUROSIL"[4] | 20 | 7.0 | 8.1 |
| 7 | 54.0 | 24.5 | "OX-50"[5] | 20 | 6.8 | 6.7 |
| 8 | 54.0 | 24.5 | Treated "OX-50"[6] | 20 | 3.9 | 9.4 |
| 9 | 54.0 | 24.5 | Quartz[7] | 20 | 8.4 | 6.9 |

[1]"IMSIL A-25" Quartz filler (Illinois Minerals).
[2]NM = not measured
[3]"VICRON" calcium carbonate (Pfizer Corp.).
[4]"DUROSIL" silica (North American Silica Co.).
[5]"OX-50" pyrogenic silica (Degussa).
[6]"OX-50" pyrogenic silica treated with gamma-methacryloxypropyl trimethoxysilane.
[7]quartz treated with gamma-methacryloxypropyl trimethoxysilane.

EXAMPLE 3

An aliphatic segmented thermoplastic polyester was prepared by measuring out the ingredients set out below in TABLE III:

TABLE III

| Ingredient | Parts |
|---|---|
| Poly(tetramethylene ether) diol[1] | 49.53 |
| Adipic acid | 29.21 |
| 1,6-hexanediol | 21.26 |
| Antioxidant[2] | 0.10 | prepared by transferring the ingredients set out below in TABLE IV to a glass vessel heated to 80° C.:

TABLE IV

| Ingredient | Parts |
|---|---|
| Segmented polyester | 80.0 |
| Urethane acrylate | 20.0 |
| CPQ | 0.25 |
| EDMAB | 0.50 |

The ingredients were heated until molten and mixed thoroughly with a spatula until homogeneous. The resultant blend was cast into a sheet and cooled, yielding a thermoplastic elastomer.

The neat segmented polyester and the segmented polyester/acrylate blend were evaluated by measuring viscosity, modulus, and shrinkage as described above. In addition, compression set was evaluated using a modified version of ADA Test Specification No. 19. Each composition was heated to 80° C. until molten and transferred to the standard compression set cylindrical mold prescribed in the Test Specification. The mold endplates were clamped into place and the mold and its contents cooled in a 22° C. water bath for 5 minutes. The resulting solidified model was removed from the mold. Each model was axially compressed 1.0 mm for 30 seconds using a metered screw clamp. The clamp was released and a measurement of permanent deformation recorded one minute later. The percentage change in cylinder height was calculated to determine compression set.

Strain-in-compression was evaluated using a modified version of ADA Test Specification No. 19. Cylindrical models were prepared according to the compression set test described above. The cylinder height was measured, a 1.125 kg mass was placed atop the cylinder, and a second height measurement was recorded thirty seconds later. The percentage change in cylinder height was calculated to determine strain-in-compression.

The results for each composition are set out below in TABLE V:

EXAMPLE 5

Inlay accuracy was evaluated by heating the molding compositions of Runs 8–11 of TABLE I and Runs 1 and 2 of TABLE V to 65° C., and using the resulting molten compositions to make an impression of a Class II MOD preparation on the lower left first molar of a "TYPODONT" model (Columbia Dentoform Corp.). The molten compositions were applied evenly to the second premolar, the prepared first molar and the second molar, and pressed into place using finger pressure while in the transparent, molten state. Each composition was cooled for 60 seconds using a stream of cold water and then removed from the TYPODONT model yielding a completed opaque impression. A standard gypsum "stone" model was poured in each impression. The hardened stone model was easily removed from the impression by slightly warming the impression to about 60° C. in a water bath. An inlay was fabricated on each stone model in the following manner. A thin film of room-temperature vulcanizing silicone ("IMPRINT", 3M) was applied to the MOD preparation on the stone model and allowed to cure. Light curable restorative material ("SILUX PLUS", 3M) was tamped into the MOD preparation and shaped and carved to provide proper fit and anatomy. The restorative material was irradiated with a VISILUX 2 curing lamp for 60 seconds. The resulting photohardened inlays were removed from the stone model and evaluated for overall fit on the original TYPODONT model preparation. Inlays were rated by two evaluators as providing excellent

TABLE V

| Run no. | Polyester/ acrylate ratio | Viscosity, 65° C. kilopoise | Modulus, 30° C. dyne/cm$^2$ × 10$^8$ | | Dimensional stability, % shrinkage | | Compression set, % | Strain-in-compression, % |
|---|---|---|---|---|---|---|---|---|
| | | | NIR[1] | IR Hot[2] | NIR | IR Hot | | |
| 1 | 100/0 | 2.7 | 0.5 | NM[3] | 0.25 | NM | 0.96 | 0.63 |
| 2 | 80/20 | 2.2 | 0.6 | 0.8 | 0.23 | 0.12 | 0.84 | 1.78 |

[1]"NIR" = Not irradiated.
[2]"IR Hot" = Irradiated hot.
[3]"NM" = Not measured.

EXAMPLE 4

Three compression set cylinders were prepared from the polycaprolactone/acrylate blend of Run 7 of TABLE I, and evaluated for compression set as in EXAMPLE 3. However, one cylinder was irradiated with a "VISILUX 2" curing light through the clamped clear plastic endplates while the composition was in the molten state. The second cylinder was irradiated after the composition had been cooled and removed from the cylindrical mold. The third cylinder was not irradiated. The three cylinders were each removed from the mold and evaluated for hot custom memory in the following manner. Each cylinder was independently placed in an 80° C. water bath for 5 minutes. The unirradiated cylinder melted and failed to maintain its cylindrical shape. Both of the irradiated cylinders exhibited only softening to an elastomeric condition. Each of the irradiated cylinders was measured lengthwise, axially compressed 2.4 mm and cooled while compressed so that a semi-permanent 2.4 mm lengthwise distortion was imparted. The cylinders were then reheated in an 80° C. water bath for 5 minutes, allowed to cool until solid and then measured lengthwise for comparison to the original cylinder length prior to compression. The cylinder irradiated in the solid state exhibited 99.86% recovery, and the cylinder irradiated in the molten state exhibited 99.75% recovery. These irradiated samples thus exhibited excellent hot custom memory, whereas the unirradiated cylinder exhibited no memory.

("++"), acceptable ("+"), or unacceptable ("–") fit. The results are set out below in TABLE VI:

TABLE VI

| Table no. | Run no. | Thermoplastic/ acrylate ratio | Inlay fit | | | |
|---|---|---|---|---|---|---|
| | | | NIR[1] | IR Hot[2] | IR Cold-IO[3] | IR Cold-EO[4] |
| I | 8 | 70/30 | ++ | ++ | +/++ | +/– |
| I | 9 | 55/45 | – | – | ++ | ++ |
| I | 10 | 70/30 | – | ++ | – | – |
| I | 11 | 55/45 | – | ++ | ++ | ++ |
| V | 1 | 100/0 | ++ | NM[5] | NM | NM |
| V | 2 | 80/20 | ++ | ++ | NM | NM |

[1]"NIR" = Not irradiated.
[2]"IR Hot" = Irradiated hot.
[3]"IR Cold-IO" = Irradiated cold "intraorally" (while on model).
[4]"IR Cold-EO" = Irradiated cold "extraorally" (after removal from model).
[5]"NM" = Not measured.

The above data illustrates a variety of techniques for preparing inlays from compositions of the invention. For some compositions, excellent inlay fit was obtained even though irradiation was not carried out until after the composition had been cooled to a solid state and removed from the model.

EXAMPLE 6

A filled thermoplastic custom tray composition was prepared by combining 22.5 parts "TONE P-767" polycaprolactone, 7.5 parts "SR-9505" urethane diacrylate, 1.2 parts "EBERCRYL 830" polyester hexacrylate, 45 parts "VICRON" calcium carbonate (Pfizer Corp.), 10 parts "SIPERNAT D-11" treated precipitated silica (North American Silica Co.), 5 parts "ULTRASIL VN-SP3" untreated precipitated silica (North American Silica Co.), 4 parts "1156" chopped glass fibers (PPG), and 0.75 parts each CPQ and EDMAB. The ingredients were stirred in a warm vessel at about 100° C. until homogeneous. The resulting mixture was cast atop polyester film into a 2.5 mm thick sheet into which was pressed a web of "SONTARA 8000" nonwoven material (E.I. DuPont de Nemours & Co.). The warm sheet was cut into generally U-shaped pieces using a "cookie cutter" style cutting implement. Each piece was squeezed while still warm between two halves of a silicone mold to form an arch-shaped, nonwoven web-lined customizable tray. The tray could be reheated and shaped while warm to conform to a patient's dentition. When irradiated for two minutes in a "STAR-CURE" curing chamber (Star X-ray, Inc.), a tray with hot custom memory was obtained. The tray can also be photocured by setting it under a conventional dental operatory light (for example, a "RITTER STAR LIGHT", Sybron Corp.) for about two minutes per side.

EXAMPLE 7

Using the method of EXAMPLE 1, a photosettable thermoplastic composition was prepared by mixing the ingredients set out below in TABLE VII:

TABLE VII

| Ingredient | Parts |
| --- | --- |
| "TONE P-767" Polycaprolactone | 59.40 |
| "SR-9505" Urethane diacrylate | 39.60 |
| CPQ | 0.50 |
| EDMAB | 0.50 |

The resulting thermoplastic composition is useful as a crown and bridge material. A bridge was prepared in the following manner. The thermoplastic composition was transferred to a syringe and placed in a 70° C. water bath for about 5 minutes. The second molar was removed from a "TYPODONT" model, and the adjacent first and third molars were prepared as abutment teeth. The thermoplastic composition was syringed onto the abutment teeth and into the gap between them. The composition was shaped while warm to form a bridge with appropriate anatomical form. The bridge was then irradiated for 30 seconds with a "VISILUX 2" curing light. The bridge was allowed to cool, removed from the model and irradiated thoroughly for an additional 60 seconds. The bridge could be firmly reseated on the model. It could be adhered intraorally to actual abutment teeth using a standard dental adhesive such as "SCOTCH-BOND" Dual Cure adhesive (3M).

EXAMPLE 8

A crown was fabricated from the composition of EXAMPLE 7. The resulting crown was fairly rigid and could be bonded to a prepared tooth using a standard dental adhesive or cement.

EXAMPLE 9

Using the method of EXAMPLE 1, a photosettable thermoplastic custom tray was fabricated from a composition prepared by mixing together the ingredients set out below in TABLE VIII:

TABLE VIII

| Ingredient | Parts |
| --- | --- |
| "TONE P-767" Polycaprolactone | 27.0 |
| "CMD 8805" Urethane diacrylate | 12.3 |
| CPQ | 0.5 |
| EDMAB | 0.5 |
| "IMSIL A-25" Filler | 10.0 |

The resulting thermoplastic composition was fabricated into a partially formed tray having a half-moon shape and a protruding handle at the midline. The tray (excluding its handle) was suspended in a 70° C. water bath until transparent, then shaped to fit around the full arch of a "TYPODONT" model. The tray was allowed to cool slightly and then removed from the model. The resulting custom tray was uniformly irradiated with a "VISILUX 2" curing light for about 2 minutes, yielding a rigid photoset tray. The tray was placed in an 80° C. oven for 10 minutes. It retained its shape without slumping, thus illustrating the heat resistance imparted by hot custom memory.

"EXPRESS" tray adhesive (3M) was applied to the photoset custom tray with a brush and allowed to dry for about 5 minutes. "IMPRINT" single phase impression material (3M) was syringed onto the model and into the tray. The tray was reseated on the model and the impression material allowed to set for about 5 minutes. Upon removal of the tray from the model the impression material remained firmly adhered to the tray.

EXAMPLE 10

Using the method of EXAMPLE 9, an unirradiated customizable tray was prepared and placed in a resealable polyethylene bag of dimensions slightly greater than the tray. The bag was immersed in 70° C. water until the full arch portion of the tray was transparent. The bag was removed from the water, and the bay and tray shaped to fit the full arch of a "TYPODONT" model. After cooling, the custom tray was easily removed from the bag. The bag serves as a convenient custom tray enclosure that discourages mess and contamination, and serves as a spacer between the dental tissue and tray. The spacer allows clearance for adequate amounts of impression material when a final impression is formed.

EXAMPLE 11

A dental die stone substitute was prepared by blending the ingredients set out below in TABLE IX:

TABLE IX

| Ingredient | Parts |
| --- | --- |
| "TONE P-300" Polycaprolactone | 39.3 |
| "CMD 8805" Urethane diacrylate | 9.8 |
| CPQ | 0.5 |
| EDMAB | 0.5 |
| "EBERCRYL 830" Polyester hexacrylate | 0.8 |
| "VICRON" Calcium carbonate | 49.1 | at 80° C. until homogeneous. The resulting low viscocity thermoplastic molding composition was tranferred to a syringe and delivered while warm into an inverted silicone elastomer full arch impression of a "TYPODONT" model. The impression was filled to above the gumline. The composition was irradiated on its back (gum) side only for 2 minutes with a "STAR-CURE" curing unit and transferred to a cold water bath for 2 additional minutes. The solildified model was removed from the silicone elastomer, yielding a rigid, highly detailed reproduction of the dentition. The solidified model was irradiated for an additional 2 minutes, yeilding a model with excellent hot custom memory.

Although this invention has been described using certain illustrative examples, it should be understood that the invention is not limited to the specific exemplary embodiments shown in this specification.

We claim:

1. A dental crown or bridge, said crown or bridge being formed from a composition comprising a thermoplastic, free radically polymerizable material and a free-radical initiator, the composition being solid at 38° C. and having a melting or softening point at a temperature less than 75° C., the composition having semi-thermoplasticity and hot custom memory after the material is polymerized.

2. A dental crown or bridge according to claim 1, wherein the composition has a melting or softening temperature less than about 65° C.

3. A dental crown or bridge according to claim 1, wherein the material has been polymerized.

4. A dental crown or bridge according to claim 1, wherein the composition has been photopolymerized.

5. A dental crown or bridge according to claim 1, wherein the composition will maintain its shape at an elevated temperature sufficient to melt or soften the composition before the material was photopolymerized.

6. A dental crown or bridge according to claim 1, wherein the composition comprises an acrylate or methacrylate.

7. A dental crown or bridge according to claim 1, wherein the composition comprises an unsaturated amide.

8. A dental crown or bridge according to claim 1, wherein the composition comprises an acrylated urethane oligomer or polymer.

9. A dental crown or bridge according to claim 1, wherein the material comprises an acrylated polyester oligomer or polymer.

10. A dental crown or bridge according to claim 1, wherein the initiator comprises a photoinitiator.

11. A method for making a crown or bridge, comprising the steps of:

a) heating a molding composition to a molten or softened state, said composition comprising a thermoplastic, free-radically polymerizable material, and a free-radical initiator, the composition being solid at 38° C. and having a melting or softening point that comfortably can be withstood by oral tissues, b) shaping said molten or softened molding composition to the form of a crown or bridge, and in either order, c) cooling the composition so that it solidifies and d) causing or permitting the free-radically polymerizable material to undergo polymerization, whereby a semi-thermoplastic crown or bridge having hot custom memory is obtained.

12. The product made by the process of claim 11.

* * * * *